United States Patent
Froom et al.

(10) Patent No.: US 6,794,535 B2
(45) Date of Patent: Sep. 21, 2004

(54) ESTER SYNTHESIS

(75) Inventors: Simon Frederick Thomas Froom, Snaith (GB); Stephen Robert Hodge, Beverley (GB); Witold Franciszek Pacynko, Beverley (GB)

(73) Assignee: BP Chemicals Limited, London (GB)

( * ) Notice: Subject to any disclaimer, the term of this patent is extended or adjusted under 35 U.S.C. 154(b) by 128 days.

(21) Appl. No.: 09/752,834

(22) Filed: Jan. 3, 2001

(65) Prior Publication Data

US 2001/0029307 A1 Oct. 11, 2001

Related U.S. Application Data

(63) Continuation of application No. PCT/GB99/02101, filed on Jul. 1, 1999.

(30) Foreign Application Priority Data

Jul. 14, 1998 (GB) .............................................. 9815135

(51) Int. Cl.[7] .......................... C07C 67/04; C07C 67/00; C07C 67/48
(52) U.S. Cl. ......................... 560/247; 560/241; 560/248
(58) Field of Search ................................ 560/247, 241, 560/248

(56) References Cited

U.S. PATENT DOCUMENTS

| | | | | |
|---|---|---|---|---|
| 3,644,497 A | * | 2/1972 | Mesich | ........................ 560/247 |
| 4,205,182 A | * | 5/1980 | Izumi et al. | ................ 560/247 |
| 4,405,808 A | * | 9/1983 | Nakajima et al. | ............ 560/247 |
| 4,465,852 A | * | 8/1984 | Sato | ............................ 560/247 |
| 4,927,954 A | * | 5/1990 | Knopf et al. | ................ 558/441 |
| 5,217,603 A | | 6/1993 | Inoue et al. | |
| 5,241,106 A | * | 8/1993 | Inoue et al. | ................ 560/247 |
| 5,457,228 A | | 10/1995 | Tokumoto et al. | |
| 5,466,876 A | | 11/1995 | McClarron et al. | |

FOREIGN PATENT DOCUMENTS

| | | |
|---|---|---|
| EP | 0 562 139 A1 | 9/1993 |
| EP | 0 757 027 A1 | 2/1997 |
| EP | 0757027 A1 * | 2/1997 |
| JP | 59231027 A | 12/1984 |
| JP | 61204148 A | 9/1986 |
| JP | 7-17907 * | 1/1995 |

OTHER PUBLICATIONS

BP Chemicals Ltd.; Communication Pursuant to Article 115(2) EPC; BPCL 8935; 99929534.8–2103/1097121.
Chemical Engineering Developments 15; Catalyst Design; Publ. by Maki Shoten, Oct. 15, 1981.
Chemical Engineering Developments 15; Catalyst Design; Publ. by Maki Shoten, Oct. 15, 1981.

* cited by examiner

Primary Examiner—Ba K. Trinh
Assistant Examiner—Taylor Victor Oh
(74) Attorney, Agent, or Firm—Nixon & Vanderhye

(57) ABSTRACT

Process for the production of lower aliphatic esters comprising reacting a lower olefin with a saturated lower aliphatic monocarboxylic acid in the vapor phase in the presence of a heteropolyacid catalyst. The reaction is carried out in a plurality of reactors set up in series, and the feedstock is rendered substantially free of metallic or metal compound impurities prior to being brought into contact with the heteropolyacid catalyst.

14 Claims, No Drawings

ESTER SYNTHESIS

This application is a continuation of PCT/GB99/02101 filed Jul. 1, 1999.

The present invention relates to a process for the synthesis of esters by reacting an olefin with a lower carboxylic acid in the presence of an acidic catalyst.

It is well known that olefins can be reacted with lower aliphatic carboxylic acids to form the corresponding esters. One such method is described in GB-A-1259390 in which an ethylenically unsaturated compound is contacted with a liquid medium comprising a carboxylic acid and a free heteropolyacid of molybdenum or tungsten. This process is a homogeneous process in which the heteropolyacid catalyst is unsupported. A further process for producing esters is described in JP-A-05294894 in which a lower fatty acid is esterified with a lower olefin to form a lower fatty acid ester. In this document, the reaction is carried out in the gaseous phase in the presence of a catalyst consisting of at least one heteropolyacid salt of a metal eg Li, Cu, Mg or K, being supported on a carrier. The heteropolyacid used is phosphotungstic acid and the carrier described is silica.

We have now discovered that metallic or metal compound impurities present in the reactants and any inert gases used in the reaction have a tendency to deactivate the acid catalyst. In particular, the presence of, for example, iron, chromium, molybdenum and nickel arising from the corrosion of equipment and sodium/potassium (if present in significant amounts) or calcium from any water or acetic acid reactant used are detrimental to the heteropolyacid catalyst. These impurities may contaminate the catalyst either by entrainment in the vapour streams or as gas phase acetate salts in the vapour stream.

Accordingly, the present invention is a process for the production of lower aliphatic esters which comprises reacting a lower olefin with a saturated lower aliphatic mono-carboxylic acid in the vapour phase in the presence of a heteropolyacid catalyst, characterised in that a) the reaction is carried out in a plurality of reactors set up in series, and b) the feedstock is rendered substantially free of metallic or metal compound impurities substances prior to being brought into contact with the heteropolyacid catalyst.

By using a gaseous feedstock substantially free of such impurities, the process efficiency can be improved significantly.

By the expression "substantially free of metallic or metal compound impurities" is meant here and throughout the specification that the total feed to the reactor has no more than 0.1 ppm of metals and/or metal compounds, preferably less than 0.01 ppm, prior to being brought into contact with the catalyst so as to enhance acceptable catalyst life. The feedstock to the reactor is made up of fresh and recycled components.

The metallic and metal compound impurities in particular are detrimental to the acid catalyst and cause deactivation. Specific examples of such impurities include the metals iron, chromium, nickel, sodium, potassium and calcium and compounds thereof Impurities such as iron, chromium, molybdenum or nickel usually arise from the corrosion of equipment whereas those of sodium, potassium or calcium result from any water or acetic acid reactant used in the reaction. In particular, these have a tendency to build up in recycle streams, especially in the acid recycle because they are carried over in the vaporiser.

These impurities may be removed from the feed to the reactor using a guard bed or, preferably, a vaporiser. Where a guard bed is used, this could be in the form of a resin which is added to the liquid streams whether they be fresh feeds or recycle streams before these are vaporised. The guard bed suitably contains an ion-exchange resin through which the liquid streams pass so as to entrap the metallic or metal compound impurity present. Other materials which can be used as a guard bed include amorphous aluminosilicates, clays, zeolites, aluminophosphates, silicoaluminophosphates, metalaluminophosphates and supported heteropolyacids. Specific examples of resins are eg Amberlyst® 15H, Purolite® CT 145 and CT 175. Since the impurities are likely to build up above the specified threshold levels in any streams being recycled to the reaction, such recycle streams should also be passed through the guard bed in order to minimise contamination of the catalyst by adventitious entry of metal/metal compound impurities into the reactor.

Where a vaporiser is employed, it may be designed to minimise carry over of these metallic impurities by using demister pads and/or using a heavy ends take-off at the base of the vaporiser where most of the metal salts will be removed. The design of the vaporiser can be such that fresh acid, which is low in heavy metals, can be fed in at the top of the reactor to scrub out metals. This would improve the efficiency of metal removal.

In one embodiment, both a guard bed and a vaporiser are employed to remove metal impurities from the feedstock. The feedstock is first passed through a guard bed as described above, and the liquid exiting the bed (ie the eluate) is introduced into a middle and/or upper region of the vaporiser. For example, where a 5-tray vaporiser is employed, the eluate may be passed to tray 2 (from the top). Ethylene reactant may then be fed into the bottom of the same vaporiser, whereby the acid, and any recycle streams fed thereto are vaporised. The vaporiser suitably contains a liquid demister at or above the top tray to minimise any liquid carry over. Fresh acetic acid is suitably fed above the top tray of the vaporiser to scrub the vapours of recycled acid as it rises up the vaporiser thereby preventing any heavy metal carry over along with the vaporised acid and ethylene.

Ethylene saturated with vaporised acid (and any water) emerging from the vaporiser may be suitably further heated before being fed to the plurality of reactors.

In the reaction, the olefin reactant used is suitably ethylene, propylene or mixtures thereof. Where a mixture of olefins is used, the resultant product will inevitably be a mixture of esters. The source of the olefin reactant used may be a refinery product or a chemical grade olefin which invariably contains some alkanes admixed therewith. The other feedstock such as acid, water and recycle streams, in particular, may contain metal or metal compound impurities which have to be removed as described above prior to being brought into contact with the acid catalyst.

The saturated, lower aliphatic mono-carboxylic acid reactant is suitably a C1–C4 carboxylic acid and is preferably acetic acid.

The reaction is carried out in a plurality of reactors set up in series such that the reactant gases exiting from a first reactor are fed as the feed gas to a second reactor and so on for subsequent reactors, and an aliquot of the reactant monocarboxylic acid is introduced into the feed gas to the second and subsequent reactors so as to maintain the olefin to monocarboxylic acid ratio in the feed gas to each of the second and subsequent reactors within a pre-determined range.

Thus, the mole ratio of olefin to the lower monocarboxylic acid in the reactant gases fed to the first reactor is suitably in the range from 1:1 to 18:1, preferably from 10:1 to 14:1.

During the reaction, when the reactant gases come into contact with the heteropolyacid in a catalyst bed, at least some of the acid is used up to form the ester in an exothermic reaction and the mole ratio of olefin to monocarboxylic acid increases considerably from a starting ratio of 12:1 to about 30:1 in the exit gases from the final reactor. As the reaction is carried out in a plurality of reactors set up in series, the exit gases from the first reactor are fed as the feed gas to the second reactor and the exit gases from the second reactor are fed as the feed gas to the third reactor and so on. The olefin to monocarboxylic acid mole ratio in the feed gas to the second and subsequent reactors is seriously depleted due to the acid being used up in the formation of the ester. This mole ratio of olefin to monocarboxylic acid is brought to the desired range by injecting further aliquots of the monocarboxylic acid to the feed gas prior to its entry into each of the second and subsequent reactors. In the case of the manufacture of ethyl acetate from ethylene and acetic acid, this range of mole ratios of ethylene to acetic acid in the reactant gases fed to the first reactor is suitably in the range from 1:1 to 18:1, preferably from 10:1 to 14:1 and that of the feed gas to the second and subsequent reactors is suitably from 10:1 to 16:1. The addition of further aliquots of the monocarboxylic acid to the feed gas to the second and subsequent reactors should be sufficient to bring the mole ratio of the olefin to acid within this range of 10:1 to 16:1.

The plurality of reactors set up in series referred to above need not be a descrete set of individual reactors. The process of the present invention may work equally as effectively if the reaction is carried out in one long reactor which has a plurality of catalyst beds set up in series and the acid is injected into the exit gases from the first bed to maintain the range of olefin to monocarboxylic acid within the predetermined range in the second and subsequent stages. In a typical reaction it is desirable to use about four reactors set up in series although this can be reduced or increased without adversely affecting the beneficial effect of the injection of the monocarboxylic acid to the feed gas to the second and subsequent catalyst beds or reactors.

The reactors used in this context are suitably run under adiabatic conditions. Due to the exothermic nature of the reaction, it may be necessary to cool the feed gases to the second and subsequent reactors so as to maintain the reaction temperature within the desired range. This cooling may be achieved either by inserting an intermediate cooling step between the each of the reactors and can be wholly or partially replaced by the injection of the acid into the feed gas to the second and subsequent reactors. The intermediate cooling step can also be used where a single long reactor which has a plurality of catalyst beds set up in series is used. In this latter case, the intermediate cooling step is used to cool the reactant gases entering the second and subsequent catalyst beds. Where a cooling step is used, this may be achieved eg by using one or more of heat exchanger tubes and by injection of the additional monocarboxylic acid reactant into the feed gases as described above.

The process of the present invention can be improved further by the addition of water as a component of the reaction mixture. The water added to the reaction mixture is suitably present in the form of steam and is capable of generating a mixture of esters-and alcohols in the process. It has been found that the presence of water in the reaction mixture in an amount of 1–10 mole %, preferably from 3 to 7 mole %, eg 5 to 6.5 mole % (based on the total moles of acetic acid, olefin and water) enhances the stability of the catalyst and thereby enhances the efficiency of the process. Furthermore, the presence of water also reduces the selectivity of the process to undesired by-products such as eg oligomers and other unknowns, excluding diethyl ether and ethanol. Water addition may also be used to supplement the cooling of the feed gases to the second and subsequent reactors.

It has further been found that dosing the reaction mixture with amounts of a di-ether such as eg diethyl ether, as a co-feed also reduces the formation of undesirable by-products. The amount of di-ether co-fed is suitably in the range from 0.1 to 6 mole %, preferably in the range from 0.1 to 3 mole % based on the total reaction mixture comprising the olefin, the aliphatic carboxylic acid, water and diethyl ether. The di-ether co-fed may correspond to the by product di-ether from the reaction generated from the reactant olefin. Where a mixture of olefins is used, eg a mixture of ethylene and propylene, the di-ether may in turn be an unsymmetrical di-ether. The di-ether co-feed may thus be the by-product of the reaction which by-product is recycled to the reaction mixture.

The term "heteropolyacid" as used herein and throughout the specification in the context of the catalyst is meant to include the free acids. The heteropolyacids used to prepare the esterification catalysts of the present invention therefore include inter alia the free acids and co-ordination type partial acid salts thereof in which the anion is a complex, high molecular weight entity. Typically, the anion comprises 2–18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for instance, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field and are known eg as Keggin, Wells-Dawson and Anderson-Evans-Perloff structures.

Heteropolyacids usually have a high molecular weight eg in the range from 700–8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be used as the catalysts in the present invention include:

| | |
|---|---|
| 12-tungstophosphoric acid | $H_3[PW_{12}O_{40}].xH_2O$ |
| 12-molybdophosphoric acid | $H_3[PMo_{12}O_{40}].xH_2O$ |
| 12-tungstosilicic acid | $H_4[SiW_{12}O_{40}].xH_2O$ |
| 12-molybdosilicic acid | $H_4[SiMo_{12}O_{40}].xH_2O$ |
| Cesium hydrogen tungstosilicate | $Cs_3H[SiW_{12}O_{40}].xH_2O$ |

The heteropolyacid catalyst whether used as a free acid or as a partial acid salt thereof is suitably supported, preferably on a siliceous support. The siliceous support is suitably in the form of granules, beads, agglomerates, globules, extrudates or pellets.

The siliceous support used can be derived from an amorphous, non-porous synthetic silica especially fumed silica, such as those produced by flame hydrolysis of $SiCl_4$. Specific examples of such siliceous supports include Support 350 made by pelletisation of AEROSIL® 200 (both ex Degussa). This pelletisation procedure is suitably carried out by the process described in U.S. Pat. No. 5,086,031 (see especially the Examples) and is incorporated herein by reference. Such a process of pelletisation or extrusion does not involve any steam treatment steps and the porosity of the support is derived from the interstices formed during the pelletisation or extrusion step of the non-porous silica The silica support is suitably in the form of pellets or beads or are globular in shape having an average particle diameter of 2 to 10 mm, preferably 4 to 6 mm. The siliceous support suitably has a pore volume in the range from 0.3–1.2 ml/g, preferably from 0.6–1.0 ml/g. The support suitably has a crush strength of at least 2 Kg force, suitably at least 5 Kg force, preferably at least 6 Kg and more preferably at least 7 Kg. The crush strengths quoted are based on average of that determined for each set of 50 beads/globules on a CHATTILLON tester which measures the minimum force necessary to crush a particle between parallel plates. The bulk density of the support is suitably at least 380 g/l, preferably at least 440 g/l.

The support suitably has an average pore radius (prior to use) of 10 to 500 Å preferably an average pore radius of 30 to 100 Å.

In order to achieve optimum performance, the siliceous support is suitably free of extraneous metals or elements which might adversely affect the catalytic activity of the system. The siliceous support suitably has at least 99% w/w purity, ie the impurities are less than 1% w/w, preferably less than 0.60% w/w and more preferably less than 0.30% w/w.

Other silica supports are the Grace 57 and 1371 grades of silica. In particular, Grace 57 grade silica has a bulk density of about 0.4 g/ml and a surface area in the range of 250–350 $m^2/g$. Grace silica grade No. 1371 has an average bulk density of about 0.39 g/ml, a surface area of about 500–550 $m^2/g$, an average pore volume of about 1.15 ml/g and an average particle size ranging from about 0.1–3.5 mm. These supports can be used as such or after crushing to an average particle size in the range from 0.5–2 mm and sieving before being used as the support for the heteropolyacid catalyst.

The impregnated support is suitably prepared by dissolving the heteropolyacid, which is preferably a tungstosilicic acid, in eg distilled water, and then adding the support to the aqueous solution so formed. The support is suitably left to soak in the acid solution for a duration of several hours, with periodic manual stirring, after which time it is suitably filtered using a Buchner funnel in order to remove any excess acid.

The wet catalyst thus formed is then suitably placed in an oven at elevated temperature for several hours to dry, after which time it is allowed to cool to ambient temperature in a desiccator. The weight of the catalyst on drying, the weight of the support used and the weight of the acid on support was obtained by deducting the latter from the former from which the catalyst loading in g/liter was determined.

Alternatively, the support may be impregnated with the catalyst using the incipient wetness technique with simultaneous drying on a rotary evaporator.

This supported catalyst (measured by weight) can then be used in the process of the invention. The amount of heteropolyacid deposited/impregnated on the support for use in the reaction is suitably in the range from 10 to 60% by weight, preferably from 20 to 50% by weight based on the total weight of the heteropolyacid and the support.

The reaction is carried out in the vapour phase suitably above the dew point of the reactor contents comprising the reactant acid, any alcohol formed in situ, the product ester and water as stated above. Dew point is the temperature at which condensation of a vapour of a given sample in air takes place. The dew point of any vaporous sample will depend upon its composition. The supported heteropolyacid catalyst is suitably used as a fixed bed in each reactor which may be in the form of a packed column. The vapours of the reactant olefins and acids are passed over the catalyst suitably at a GHSV in the range from 100 to 5000 per hour, preferably from 300 to 2000 per hour.

The reaction is suitably carried out at a temperature in the range from 150–200° C. within which range the entry temperature of the reactant gases is suitably from 160–180° C. and the temperature of the exit gases from each reactor is suitably 170–200° C. The reaction pressure is suitably at least 400 KPa, preferably from 500–3000 Kpa, more-preferably about 1000 Kpa depending upon the relative mole ratios of olefin to acid reactant and the amount of water used.

The products of the reaction are recovered by eg fractional distillation. The esters produced, whether singly or as mixture of esters, may be hydrolysed to the corresponding alcohols or mixture of alcohols in relatively high yields and purity.

The process of the present invention is particularly suited to making ethyl acetate from ethylene and acetic acid by an addition reaction with optional recycle of any ethanol or diethyl ether formed.

The present invention is further illustrated with reference to the following Examples:

EXAMPLES

In the examples STY is the space time yield measured in g EtAc/l catalyst/hour

Catalyst Preparation:

Silica-granules (Grace 57 grade, surface area 310 $m^2/g$, bulk density 0.4 g/ml, pore volume 1.03 ml/g, ca. 5–8 mm, 9.3 kg, ex W R Grace) were soaked in a solution of silicotungstic acid $[H_4SiW_{12}O_{40}.26H_2O]$ (32 kg of 26% w/w aqueous solution) in order to impregnate the silica support with the silicophosphoric acid catalyst. After this duration, excess catalyst solution was drained off. The resultant catalyst impregnated support granules were then dried using a warm nitrogen stream to give a catalyst with a loading of 140 g/liter.

Catalyst Testing:

Three reactors, designed to simulate an adiabatic operation, were set up in series with intercoolers. The feedstream was heated in a vaporiser and passed into the top of the first reactor at 176° C. and 1000 Kpa pressure. The exit gases from the top reactor were cooled and fed into the second reactor at 172° C. and the exist gases from this second reactor were cooled and fed into a third reactor at 168° C. The exit gases from the third reactor were cooled and passed into a vapour-liquid separator at 30° C. The vapour stream from the separator was compressed and recycled to the vaporiser. The liquid stream from the separator was reduced in pressure to atmospheric and samples were analysed by gas chromatography. The feed to the first reactor was made up of fresh and recycled components made up of ethylene (3690 g/hr), acetic acid (558 g/hr), water (147 g/hr), ethanol (EtOH, 6 g/hr), diethyl ether (28 g/hr) and ethyl acetate (EtAc, 113 g/hr). The three reactors were charged with 283 g, 430 g and 554 g respectively of the silicotungstic acid catalyst specified above.

After the initial settling in period the catalyst activity was monitored by overall STY and exotherm on the three beds

Example 1

For the period 200–400 hrs on stream the fresh acid/water feed contained 2.9 ppm calcium. Catalyst deactivation, particularly of the top bed was observed as outlined in the table below.

| Time on stream (hrs) | Overall STY (g EtAc/lcat/hr) | Exotherm on top bed (° C.) |
|---|---|---|
| 200 | 227 | 10.6 |
| 300 | 220 | 6.5 |
| 400 | 211 | 2.4 |

After this period the top bed of catalyst was removed and analysed. An average calcium level of 0.14% w/w was found.

Example 2

The top bed was replaced with fresh catalyst and a further 200 hour period monitored. The fresh acid/water feed now contained 0.6 ppm calcium.

| Time on stream (hrs) | Overall STY (g EtAc/lcat/hr) | Exotherm on top bed (° C.) |
|---|---|---|
| 650 | 212 | 12.4 |
| 850 | 209 | 10.6 |

Again the catalyst deactivated but at a substantially lower rate than in Example 1. Analysis of the catalyst gave a calcium level of <0.01% w/w.

Example 3

This example demonstrates the removal of metal ions from the feed stream.

An acetic acid stream at 78° C. and containing 17. wt % water, 7 wt % EtAc and 4 wt % EtOH were passed through a 20 cm3 Purolite® CT 145 cation resin bed at a flow rate of 190 mls/hour. The liquid entering this resin bed contained transition metals simulating the presence of corrosion metals at concentrations of 40 ppm iron, 10 ppm nickel and 10 ppm chromium.

This bed removed these corrosion metals to a concentration of less than 0.1 ppm (detection limit of the analysis method) and treated 11 kgs of feed prior to regeneration.

What is claimed is:

1. A process for the production of lower aliphatic esters which comprises reacting a lower olefin selected from the group consisting of ethylene and propylene with a $C_1$ to $C_4$ carboxylic acid in the vapour phase in the presence of a heteropolyacid catalyst selected from the group consisting of 12-tungstophosphoric, 12-molybdophosphoric, 12-tungstosilicic and 12-molybdosilicic acid, wherein a) the reaction is carried out in a plurality of reactors set up in series, and b) the feedstock has no more than 0.1 ppm of metallic or metal compound impurities prior to being brought into contact with the heteropolyacid catalyst.

2. A process as claimed in claim 1, wherein the feedstock has no more than 0.1 ppm of metals and/or metal compounds, prior to being brought into contact with the heteropolyacid catalyst.

3. A process as claimed in claim 1, wherein the feedstock has less than 0.01 ppm of metals and/or metal compounds, prior to being brought into contact with the heteropolyacid catalyst.

4. A process as claimed in claim 1, wherein the feedstock is rendered substantially free of metallic or metal compound impurities which arise from the corrosion of equipment, or which result from any water or acetic acid reactant used in the reaction.

5. A process as claimed in claim 4, wherein the metallic or metal compound impurities which arise from the corrosion of equipment comprise: iron, chromium, nickel and/or molybdenum.

6. A process as claimed in claim 4, wherein the metallic or metal compound impurities which result from any water or acetic acid reactant used in the reaction comprise sodium, potassium and/or calcium.

7. A process as claimed in claim 1, wherein the metallic or metal compound impurities are removed from the feed to the reactor using a guard bed and/or a vaporiser.

8. A process as claimed in claim 7, wherein the guard bed is in the form of an ion-exchange resin.

9. A process as claimed in claim 7, wherein the guard bed comprises amorphous aluminosilicates, clays, zeolites, aluminophosphates, silicoaluminophosphates, metalaluminophosphates or supported heteropolyacids.

10. A process as claimed in claim 1, wherein the metallic or metal compound impurities are removed from the feed to the reactor using a vaporiser which employs demister pads and/or a heavy ends take-off at the base of the vaporiser to remove said impurities.

11. A process as claimed in claim 10, wherein fresh acid is introduced into the vaporiser to scrub out the metallic or metal compound impurities.

12. A process as claimed in claim 1, wherein said lower olefin is ethylene.

13. A process as claimed in claim 1, wherein the mole ratio of olefin to the $C_1$ to $C_4$ carboxylic acid in the reactant gases fed to the first reactor is in the range of from 1:1 to 18:1.

14. A process as claimed in claim 1, wherein said plurality of reactors set up in series is in the form of one long reactor which has a plurality of catalyst beds set up in series.

* * * * *